United States Patent [19]
Johnson

[11] Patent Number: 5,147,327
[45] Date of Patent: Sep. 15, 1992

[54] HYPODERMIC NEEDLE WITH PROTECTIVE SHEATH

[76] Inventor: Gerald W. Johnson, 17115 Red Oak, #211, Houston, Tex. 77090

[21] Appl. No.: 739,325

[22] Filed: Aug. 1, 1991

Related U.S. Application Data

[62] Division of Ser. No. 462,788, Jan. 10, 1990, Pat. No. 5,049,136.

[51] Int. Cl.$^5$ .............................................. A61M 5/32
[52] U.S. Cl. ................................... 604/198; 604/263
[58] Field of Search ............... 604/198, 192, 187, 263, 604/179, 180, 272

[56] References Cited

U.S. PATENT DOCUMENTS

| | | | |
|---|---|---|---|
| 4,170,993 | 10/1979 | Alvarez | 604/263 X |
| 4,832,696 | 5/1989 | Luther et al. | 604/192 X |
| 4,878,902 | 11/1989 | Wanderer et al. | 604/192 |

Primary Examiner—John D. Yasko
Attorney, Agent, or Firm—Neal J. Mosely

[57] ABSTRACT

A hypodermic needle has a retractable tubular sheath slidably mounted on its forward end and movable relative thereto between a rearward retracted position exposing the front end of the needle and a forward protective position enclosing the front end of the needle. In one embodiment, a spring within the sheath urges the sheath to the forward protective position enclosing the front end of the needle. The rear of the sheath cooperates with pins on the needle to engage them upon relative rotation in one direction to allow rotation as a single unit to connect the needle to fluid ejection or withdrawal members. Relative rotation in the opposite direction disengages the pins allowing the sheath to be moved rearward causing the front end of the needle to protrude beyond the front end of the sheath and to lock the needle and sheath together upon further relative rotation in the opposite direction to disconnect and dispose of the needle without inadvertent injury by contact with the needle. Another embodiment has protrusions on the needle and a retractable sheath slidably mounted on the needle and movable between a rearward retracted position exposing the needle front end and a forward protective position engaging the protrusions and covering the front end of the needle. A further modification has a tubular catheter slidably received on the needle for hypodermic penetration therewith which is removably connected to the sheath whereby when the sheath and needle are removed from the catheter only the catheter remains in place.

14 Claims, 3 Drawing Sheets

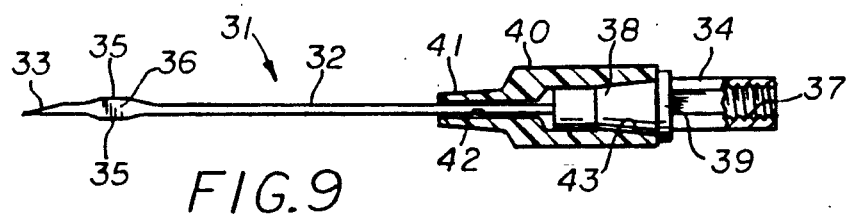
FIG. 9
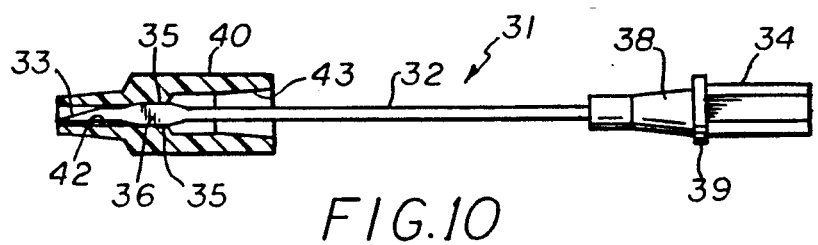
FIG. 10
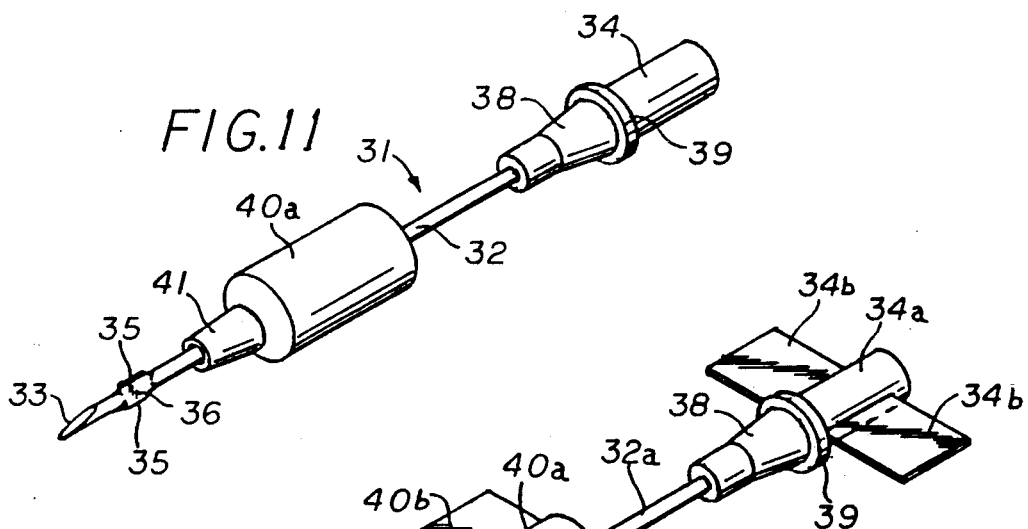
FIG. 11
FIG. 12
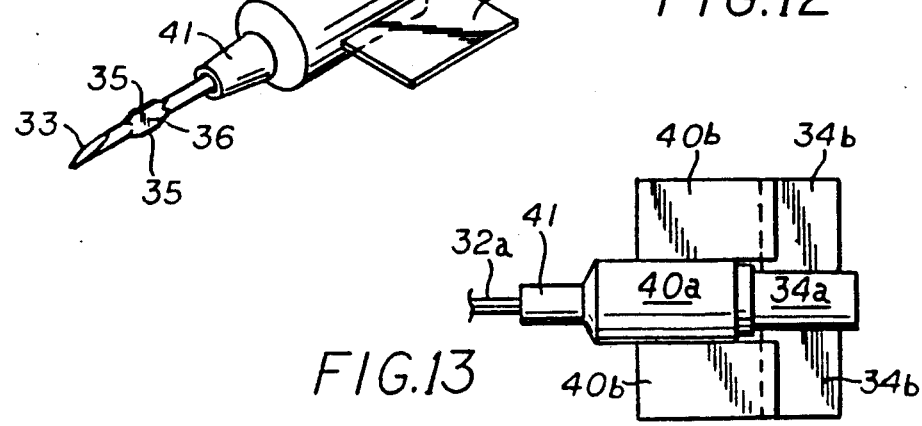
FIG. 13

HYPODERMIC NEEDLE WITH PROTECTIVE SHEATH

CROSS REFERENCE TO RELATED CASE

This application is a division of copending application Ser. No. 462,788, filed Jan. 10, 1990,, now U.S. Pat. No. 5,049,136.

BACKGROUND OF THE INVENTION

1. Field of the Invention

This invention relates generally to hypodermic needles which are adapted to inject substances into humans and animals and/or to withdraw specimens therefrom, and more particularly to a hypodermic needle having a protective sheath for shielding the needle during use, storage, and disposal.

2. Brief Description of the Prior Art

The shielding of hypodermic needles is of critical concern to health practitioners from the standpoint of both handling the needle and the disposal of used needles. Accidental exposure or puncture by the sharp end of the needle can have very serious and even fatal health consequences. For example, the needle may be contaminated with diseases such as hepatitis or A.I.D.S. It is therefore desirable that the needle be shielded immediately after use with a minimum of handling and be disposed of in a reliable and efficient manner to provide protection from accidental puncture.

There are several patents which disclose apparatus for shielding a hypodermic needle against accidental puncture and for covering the needle for disposal. Most of these patents teach devices which are mounted on the dispensing syringe, and the shielding member remains in a position covering the needle after use.

A major disadvantage with these shielding devices is that the entire dispensing syringe must also be discarded along with the needle. Disposal of hazardous waste in health facilities is a precise science. Special containers are used and rigid guidelines are followed in disposal operations. Often the practitioner is charged by the weight of the hazardous materials which are to be disposed of. The cost of special handling of hazardous material is passed along to the patient. It would be desirable to provide a device which would allow the needle to be separated from the syringe whereby both members may be disposed of separately.

U.S. Pat. Nos. 3,370,588, 3,405,713, and 4,747,835 are examples of removable needle shielding devices which are manually removed and replaced by pulling them completely off of the syringe or needle base. These devices have the disadvantage of losing the shield when removed and leaving the needle exposed and also present a risk to the person doing the handling when replacing the shield.

Sampson et al, U.S. Pat. No. 4,425,120 discloses a shielded hypodermic syringe having a tubular sleeve which slides on the barrel of the syringe and is movable from a forward shielding position to a rearward non-shielding position and utilizes slots in the sleeve to lock it n either position. This device requires manually moving the shield to the shielding position and consequently there is substantial risk to the person doing the handling and the possibility of the shield being accidentally left in the non-shielding position.

U.S. Pat. Nos. 4,655,751, 4,702,738, and 4,702,739 are examples of other shield devices which are mounted on the syringe rather than on the needle and which require manual movement of the shield to the extended position. These patents also inherently present a risk to the person doing the handling and the possibility of the shield being accidentally left in the nonshielding position.

Laico et al, U.S. Pat. No. 4,804,372 teaches a protective sheath which is mounted on the hypodermic needle base. The shield device comprises a pair of telescopic tubular shields slidably mounted to the needle base. Detent locking members lock the shields in a non-retractable extended position. This device also requires manually moving the shields to the shielding position with the resultant risk to the person doing the handling and the possibility of the shield being accidentally left in the non-shielding position.

U.S. Pat. Nos. 3,073,306, and 4,816,022 are also examples of other shield devices which are mounted on the needle rather than the syringe but still require manual movement of the shield to the extended position. These devices also inherently present a risk to the person doing the handling and the possibility of the shield being accidentally left in the non-shielding position.

White, U.S. Pat. No. 2,876,770 discloses a shielded hypodermic syringe which hides the needle from view and also shields the needle after use. The shield device comprises a pair of telescopic tubular shields urged apart by a compression spring. One end of the inner member is mounted on the syringe and its other end is provided with a stop flange. The outer member is slidably received on the inner member and has a ring-like retainer mounted at its rearward end having an inwardly facing flange which engages the inner member flange in the normally extended position. The retainer ring exterior has a semicircular step portion which extends rearward. When the outer member is rotated to one position, the step portion will engage the stop pin, and when rotated to another position step portion will engage end of the syringe whereby selective exposure of the end of the needle is controlled. This device does not provide for positive locking of the outer member in a non-retractable extended position with the resultant risk of accidental retraction of the shield during handling or disposal.

Hall, U.S. Pat. No. 4,416,663 discloses a shielded, self sterilizing, hypodermic syringe comprising a pair of telescopic tubular members having a compression spring disposed therebetween. The outer member is snap fitted onto the needle and the inner member is slidably mounted within the outer member to extend outwardly beyond the forward end. The inner member is an enclosed capsule containing sterilizing material and has perforated ends. When the capsule is pressed against the skin the needle will penetrate and pass through the sterilizing material to exit the outer end on its forward motion and when the needle is withdrawn the spring will position the capsule such that the needle tip is disposed within the sterilizing material. This device also does not provide for positive locking of the outer member in a non-retractable extended position with the resultant risk of accidental retraction of the shield during handling.

The present invention is distinguished over the prior art in general, and these patents in particular by a sheathed hypodermic needle having a retractable tubular sheath slidably mounted on its forward end and movable relative thereto between a rearward retracted position exposing the front end of the needle and a forward protective position enclosing the front end of the needle. In one embodiment, a spring within the sheath urges the sheath to the forward protective position enclosing the front end of the needle. The rear of the sheath cooperates with pins on the needle to engage the pins upon relative rotation in one direction to allow rotation as a single unit to connect the needle to fluid ejection or withdrawal members. Relative rotation in the opposite direction disengages the pins to allow the sheath to be moved rearward causing the front end of the needle to protrude beyond the front end of the sheath and to lock the needle and sheath together upon further relative rotation in the same said opposite direction to disconnect and dispose of the needle without inadvertent injury by contact with the needle. Another embodiment has protrusions on the needle and a retractable sheath slidably mounted on the needle and movable between a rearward retracted position exposing the needle front end and a forward protective position engaging the protrusions and covering the front end of the needle. A further modification has a tubular catheter slidably received on the needle for hypodermic penetration therewith which is removably connected to the sheath whereby when the sheath and needle are removed from the catheter only the catheter remains in place.

SUMMARY OF THE INVENTION

It is therefore an object of the present invention to provide a sheathed hypodermic needle having a protective sheath which will automatically assume an extended protective position covering the outer end of the needle.

It is another object of this invention to provide a sheathed hypodermic needle having a protective sheath which facilitates the safe, quick, and easy installation of the needle onto and off of the end of a syringe or intravenous tube.

Another object of this invention to provide a sheathed hypodermic needle having a protective sheath which will automatically assume a locked extended protective position covering the outer end of the needle when it is removed from the end of a syringe or intravenous tube and may be safely disposed of separately from the syringe or other disposable materials.

Another object of this invention is to provide a sheathed hypodermic needle having a retractable sheath which is normally yieldingly held in an extended protective position covering the outer end of the needle.

Another object of this invention is to provide a sheathed hypodermic needle having a retractable sheath which is easily and quickly locked in an extended protective position covering the outer end of the needle to prevent accidental retraction and exposure of the end of the needle.

Another object of this invention is to provide a sheathed hypodermic needle having a retractable sheath which will prevent the needle from being reused once it has been locked into the extended position.

A further object of this invention is to provide a sheathed hypodermic needle having a retractable sheath which does not require modifications to the syringe or other instruments to which it is attached.

A still further object of this invention is to provide a sheathed hypodermic needle having a retractable sheath which is simple in design and construction, economical to manufacture and rugged and reliable in use.

Other objects of the invention will become apparent from time to time throughout the specification and claims as hereinafter related.

The above noted objects and other objects of the invention are accomplished by a sheathed hypodermic needle having a retractable tubular sheath slidably mounted thereon. A hypodermic needle has a retractable tubular sheath slidably mounted on its forward end and movable relative thereto between a rearward retracted position exposing the front end of the needle and a forward protective position enclosing the front end of the needle. In one embodiment, a spring within the sheath urges the sheath to the forward protective position enclosing the front end of the needle. The rear of the sheath cooperates with pins on the needle to engage the pins upon relative rotation in one direction to allow rotation as a single unit to connect the needle to fluid ejection or withdrawal members. Relative rotation in the opposite direction disengages the pins to allow the sheath to be moved rearward causing the front end of the needle to protrude beyond the front end of the sheath and to lock the needle and sheath together upon further relative rotation in the same said opposite direction to disconnect and dispose of the needle without inadvertent injury by contact with the needle. Another embodiment has protrusions on the needle and a retractable sheath slidably mounted on the needle and movable between a rearward retracted position exposing the needle front end and a forward protective position engaging the protrusions and covering the front end of the needle. A further modification has a tubular catheter slidably received on the needle for hypodermic penetration therewith which is removably connected to the sheath whereby when the sheath and needle are removed from the catheter only the catheter remains in place.

BRIEF DESCRIPTION OF THE DRAWINGS

FIG. 9 is a longitudinal cross section of another preferred sheathed hypodermic needle having a manually movable protective sheath shown with the sheath in the rearward retracted position exposing the front end of the needle.

FIG. 10 is a longitudinal cross section of the embodiment of FIG. 9 shown with the sheath in the forward protective position enclosing the front end of the needle.

FIG. 11 is an isometric view of the embodiment of FIG. 9 shown with the sheath in an intermediate position.

FIG. 12 is an isometric view of a "butterfly" modification of the embodiment of FIG. 9 having lateral tabs to facilitate securing the needle to the patient.

FIG. 13 is a plan view of the "butterfly" modification of FIG. 12 showing overlapped lateral tabs.

DESCRIPTION OF A PREFERRED EMBODIMENT

Figure 1:
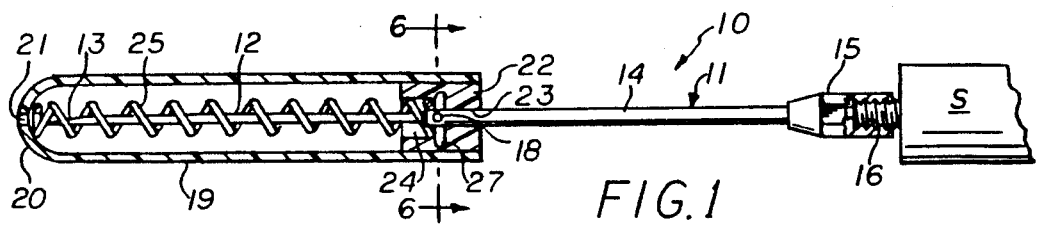
FIG. 1 is a longitudinal cross section of a preferred sheathed hypodermic needle in accordance with the present invention shown with the sheath in the forward protective position enclosing the front end of the needle.
Figure 2:
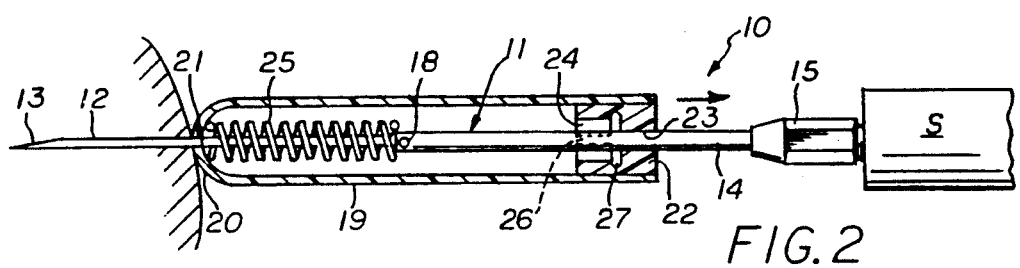
FIG. 2 is a longitudinal cross section of the sheathed hypodermic needle of FIG. 1 shown with the sheath in the rearward retracted position exposing the front end of the needle.
Figure 3:
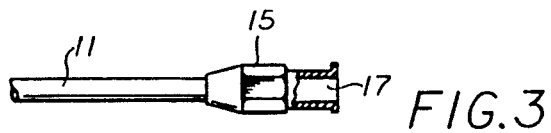
FIG. 3 is a side elevation of the rear portion of the needle body showing an alternate base configuration.

Referring to the drawings by numerals of reference, there is shown in FIGS. 1 and 2, a preferred hypodermic needle with a protective sheath 10. The tubular needle body 11 has a reduced diameter forward portion 12 with a beveled or pointed front end 13 to facilitate hypodermic insertion and an enlarged diameter rearward portion 14 having a base member 15 secured at the back end in communication with the interior of the needle. The base member 15 may be provided with internal threads 16 for threaded connection to a hypodermic syringe S. Alternatively, as shown in FIG. 3, the base member 15 may have a smooth interior bore 17 for receiving the end of an intravenous tubular member. A pair of opposed pins 18 extend transversely outward from the enlarged diameter 14 of the needle body 11 adjacent the reduced diameter forward portion 12.

A tubular sheath 19 surrounds the forward portion of the needle 11. The sheath 19 has a rounded front end wall 20 with a central aperture 21 therethrough which is of sufficient size to allow passage of the forward portion 12 of the needle 11. A cylindrical plug 22 encloses the rear end of the sheath 19. Cylindrical plug 22 (FIGS. 4 and 5) has a central bore 23 extending from the rearward end and a larger diameter bore 24 extending from the forward end coaxial therewith. Needle body 11 is slidably received through bores 23 and 24 with bore 23 slidably carried on the rearward portion 14 of needle (FIG. 5).

Figure 5:
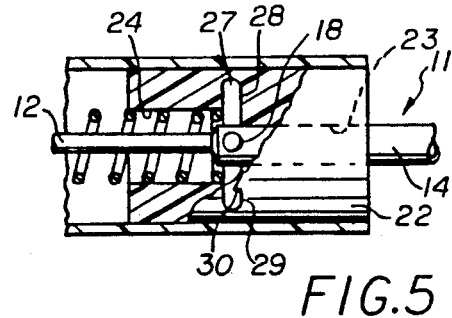
FIG. 5 is a partial enlarged longitudinal cross section of the rear portion of the sheath member showing the pin members of the needle at the rear of the slot configuration.

A compression spring 25 surrounds the forward portion of needle 11 and has one end engaged on the interior of the front end wall 20 of sheath 19 and its opposite end received within bore 24 of plug 22 and engaged on pins 18 to normally urge needle 11 rearward relative to sheath 19 whereby the front end 13 of the needle is retracted within the sheath (FIGS. 1 and 5).

Figure 4:
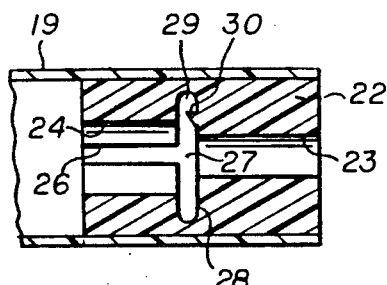
FIG. 4 is a partial enlarged longitudinal cross section of the rear portion of the sheath member showing the slot configuration with the spring and needle removed.

As best seen in FIG. 4, the plug 22 has a pair of laterally opposed slots 26 through its side wall which extend longitudinally from its front end and each terminate in a partial radial slot 27 forming a generally T-shaped guide slot on opposite sides of the plug 22. The slots 26 and 27 are of sufficient size to slidably receive the pins 18 when they are aligned with the slots.

Figure 6:
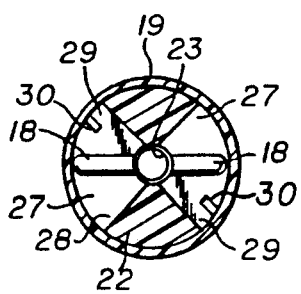
FIG. 6 is an enlarged transverse cross section of the sheathed needle taken along line 6—6 of FIG. 1 showing the pin members of the needle engaged with the sheath in the forward protective position whereby relative longitudinal and rotational movement between the needle and the sheath is allowed.
Figure 7:
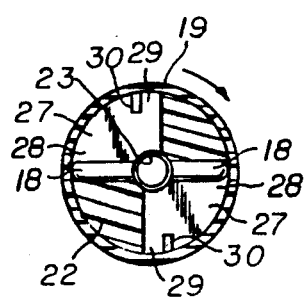
FIG. 7 is an enlarged transverse cross section of the sheathed needle showing the pin members of the needle engaged with the sheath in the forward protective position whereby relative longitudinal movement between the needle and the sheath is prevented while allowing rotational movement as a single unit in one direction about their longitudinal axis.
Figure 8:
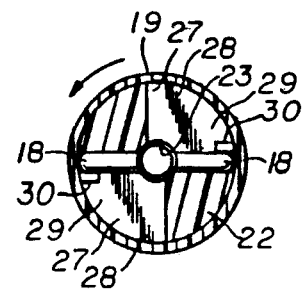
FIG. 8 is an enlarged transverse cross section of the sheathed needle showing the pin members of the needle locked within the sheath to secure the sheath in the forward protective position whereby both relative rotational and longitudinal movement between the needle and the sheath is prevented while allowing rotational movement in one direction as a single unit about their longitudinal axis to facilitate disconnection of the needle from the fluid ejection or withdrawal means.
Figure 14:
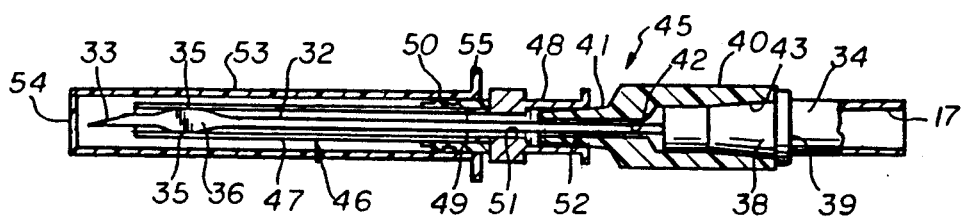
FIG. 14 is a longitudinal cross section of a preferred sheathed hypodermic catheter-needle having a manually movable protective sheath and a removable sheath enclosing the forward end of the needle and catheter.
Figure 15:
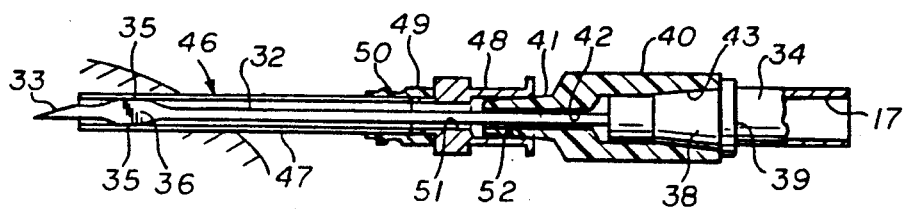
FIG. 15 is a longitudinal cross section of the catheter-needle embodiment of FIG. 14 shown with the removable sheath removed and the catheter and needle inserted into the patient.

One side 28 of each partial radial slot 27 is smoothly connected with the longitudinal slot 26 and the opposite side 29 of the radial slot 27 is provided with a restriction or protuberance, such as a barb 30 near its juncture with the longitudinal slot 26. The guide slot configuration allows the pins 18 to slide within the slot 26 (FIGS. 1, 5, and 6). As seen in FIG. 7, upon relative rotation between the sheath 19 and the needle 11 in one direction the pins 18 enter the side 28 of the slot 27. As seen in FIG. 8, when relative rotation between the members in the opposite direction is attempted, the rotation must be forced to snap the pins 18 past protuberances 30 in the slot side 29.

In this manner, spring 25 normally urge pins 18 to the rearward end of slot 26, and needle 11 and sheath 19 are rotated to position pins 18 within side slot 28, which maintains the end 13 of needle 11 retracted within sheath 19. In this position, there is no longitudinal sliding movement between needle 11 and sheath 19 and base 15 of the needle may be connected to an intravenous tube or threaded onto the end of a hypodermic syringe. In the event of a threaded connection, the needle and sheath may be rotated as a single unit in one direction (FIG. 7) to make up the threaded connection.

After the end connection is made, sheath 19 is rotated in the opposite direction to position pins 18 within longitudinal slots 26. When in this position, the sheath and needle will move longitudinally relative to one another. The end 20 of sheath 19 is placed on the surface of the skin and needle 11 is moved forward relative to the sheath to penetrate the skin. As the needle is withdrawn, spring 25 forces sheath 19 forward and the end 13 of the needle is once again retracted within the sheath. The rearward end of the needle is then disconnected from the intravenous tube or the hypodermic syringe.

As seen in FIG. 8, to disconnect a threaded connection, sheath 19 is rotated to unscrew the threads while the needle is connected to the syringe causing relative rotation between sheath 19 and needle 11. This causes pins 18 to be forced into slot side 29 past protuberances 30. Thus, relative rotation between the members in the opposite direction snaps pins 18 into the side 29. The protuberances 30 now lock pins 18 into the side 29.

This locking position can also be accomplished by grasping the sheath and the rearward end of the needle and twisting them in the opposite direction to snap pins 18 into slot side 29. Once pins 18 are secured in slot side 29, both relative rotational and longitudinal movement between the members is prevented and the end of the needle is safely retracted within the sheath. This allows the used needle to be safely handled and disposed of without the danger of accidental pricking or reuse.

MANUALLY MOVABLE EMBODIMENT

Referring to the drawings by numerals of reference, there is shown in FIGS. 9, 10, and 11, a hypodermic needle, designated generally by numeral 31 having a slidable protective sheath member which is manually movable to cover the pointed end of the needle. The hollow tubular needle body 32 has a beveled front end 33 to facilitate hypodermic insertion and a base member 34 secured at the back end in communication with the interior bore of the needle.

A pair of small laterally opposed projections 35 are formed on the exterior of needle body 32 near beveled front end 33. In a preferred embodiment, needle body 32 is slightly flattened forming a slightly flattened portion 36 and small laterally opposed projections 35 on the exterior of the needle body. The side walls of flattened portion 36 of the needle body are spaced sufficiently apart such that fluid flow through the interior of the needle body is not obstructed. It should be understood that small projections 35 may also be formed on the exterior of the needle body 111 by other conventional methods rather than by flattening such that the needle body 32 remains round.

The base member 34 may be provided with internal threads 37 for threaded connection to a hypodermic syringe, or alternatively as previously described and shown in FIG. 3, may have a smooth interior bore 17 for receiving the end of an intravenous tubular member when the needle is in use or a conventional end cap or plug (not shown) when not in use. The exterior of base member 34 has a reduced diameter front portion 38 and a radial flange 39 near the reduced diameter portion 38. The reduced diameter portion 38 is rearward and outwardly tapered.

A cylindrical protective sheath member 40 is slidably received on the exterior of needle body 23. The exterior of the protective sheath member 40 has a reduced diameter portion 41 at the forward end which tapers rearward and outwardly. The interior of the protective sheath member 40 has a small central bore 42 at the forward end and a coaxial larger bore 43 at the rearward end.

The small diameter bore 42 is sized to slide axially on the exterior of needle body 32 and in its forward position to frictionally engage the small laterally opposed projections 35 on the exterior of the needle body and is of sufficient length to cover beveled front end 33 of needle body 32. Larger bore 43 at the rearward end of protective sheath member 40 is sized and tapered rearward and outwardly to receive and engage tapered reduced diameter front portion 38 of needle base 34.

In the protective position, cylindrical protective sheath member 40 is in the forward position and frictionally engaged on small laterally opposed projections 35 on exterior of the needle body 32 to cover beveled front end 33 of the needle. In this position, there is no longitudinal sliding movement between needle 32 and protective sheath 40.

When threadedly connecting needle base 34 onto the end of a hypodermic syringe, needle 32 and protective sheath 40 may be rotated as a single unit to make up the threaded connection. After the end connection is made, the protective sheath 40 may be manually pulled to the rear position to frictionally engage it on reduced diameter portion 38 of needle base 34. When needle base 34 is connected to an intravenous tube, protective sheath 40 is moved to its rear protective position prior to hypodermic insertion into the skin.

After the needle has been used, protective sheath 40 is manually pushed to the forward position to once again frictionally engage it on small laterally opposed projections 35 on the exterior of needle body 32 to cover beveled front end 33 of the needle. In this position, the needle can be safely handled and disposed of without the danger of accidental pricking or reuse.

FIG. 12 shows a "butterfly" modification of the needle wherein the base 34a of the needle body 32a and the base of the protective sheath member 40a each have a pair of opposed flexible "wings" or tabs 34b extending laterally outward from their exterior diameters. The tabs 34b and 40b provide a flat surface to facilitate securing the needle and/or protective sheath member to the patient with tape. Each pair of flexible tabs 34b or 40b may be bent upward and pinched together with the fingertips to facilitate handling. As seen in FIG. 13, one pair of the flexible tabs may also be sized to overlap the other whereby they may be bent and pinched together as a single pair when the protective sheath member 40a is in the rear position.

CATHETER-NEEDLE EMBODIMENT

Referring to the drawings by numerals of reference, there is shown in FIGS. 14 through 18, an intravenous catheter-needle combination designated generally by numeral 45 having a sliding protective sheath which is manually movable to cover the pointed end of the needle and a removable protective sheath which covers the forward end of the needle and catheter.

As previously described with reference to FIGS. 9–11, hollow tubular needle body 32 has a beveled front end 33 to facilitate hypodermic insertion and a base member 34 secured at the back end in communication with the interior bore of the needle. A pair of small laterally opposed projections 35 are formed on the exterior of needle body 32 near beveled front end 33. In the preferred embodiment, needle body 32 is slightly flattened forming a slightly flattened portion 36 and small laterally opposed projections 35 on the exterior of the needle body. The side walls of flattened portion 36 of needle body 32 are spaced sufficiently apart such that fluid flow through the interior of the needle body is not obstructed.

It should be understood that small projections 35 may also be formed on the exterior of needle body 32 by other conventional methods rather than by flattening such that needle body 32 remains round.

Base member 34 of the catheter-needle embodiment has a smooth interior bore 17 for receiving the end of an intravenous tubular member when the needle is in use or a conventional end cap or plug (not shown) when not in use. The exterior of the base member 34 has a reduced diameter front portion 38 and a radial flange 39 near reduced diameter portion 38. The reduced diameter portion 38 is rearward and outwardly tapered.

A cylindrical protective sheath member 40 is slidably received on the exterior of needle body 32. The exterior of protective sheath member 40 has a reduced diameter portion 41 at the forward end which tapers rearward and outwardly. The interior of protective sheath member 4 has a small central bore 42 at the forward end and a coaxial larger bore 43 at the rear end. The small diameter bore 42 is sized to slide axially on the exterior of needle body 32 and in its forward position to frictionally engage the small laterally opposed projections 35 on the exterior of the needle body and is of sufficient length to cover beveled front end 33 of the needle.

The larger bore 42 at the rearward end of protective sheath member 40 is sized and tapered rearward and outwardly to receive and frictionally engage the tapered reduced diameter front portion 38 of needle base 34. When assembled and prior to use, protective sheath member 40 is in the rearward position engaged on front portion 38 of the base of the needle.

An intravenous tubular catheter 46 is slidably received on the front portion of the needle. The catheter 46 has a flexible tubular front portion 47 which is adapted for intravenous insertion and a base member 48 secured at the back end in communication with the interior of tubular portion 47. The interior diameter of tubular front portion 47 closely surrounds needle body 32 but allows axial sliding movement of needle projections 35 therethrough. An intermediate portion 49 of the catheter surrounds tubular portion 47 at its juncture with the base 48 and has an annular bead 50 on its exterior surface. The intermediate portion has a small interior diameter which engages and seals the exterior of tubular portion 47 and a reduced diameter front portion of base member 48 to join them together.

The catheter base member 48 has a small interior bore at its forward end which is sized to allow axial sliding movement of needle projections 35 therethrough and a coaxial larger interior diameter 52 at its rearward end which is sized to receive the end of an intravenous tubular member when the needle is removed or a conventional end cap or plug (not shown) when not in use. The tapered front end 41 of protective sheath member 40 is sized to be frictionally received and engaged in bore 52 of base member 48 of catheter 46. When assembled and prior to use, protective sheath member 40 is in the rearward position engaged on front portion 38 of needle base 34, and base member 48 of catheter 46 is in the rearward position engaged on front portion 41 of protective sheath member 40. The length of the catheter tubular portion 47 is slightly smaller than the length of needle 32 so that beveled front end 33 of the needle is exposed to facilitate intravenous insertion of both needle 32 and tubular portion 47 of catheter 46.

A removable tubular protective sheath 53 surrounds the forward portion of needle 32 and tubular portion 47 of catheter 46. The removable tubular sheath 53 has an enclosed front end 54 and its interior diameter is sized to receive and frictionally engage exterior bead 50 on intermediate portion 49 of catheter 46. The open end of removable sheath 53 may be provided with a radial flange 55 to facilitate installation and removal.

Thus in the completely assembled condition, the protective sheath member 40 is in the rearward position engaged on the front portion 38 of base 34 of needle 32, base member 48 of catheter 46 is in the rearward position engaged on front portion 41 of protective sheath member 40, and removable sheath 53 is frictionally engaged on bead 50 of intermediate portion 49 of catheter 46 and surrounds the forward portion of needle 32 and tubular portion 47 of catheter 46.

To use the catheter-needle combination, removable sheath 53 is removed from catheter 46. The beveled end 33 of needle 32 having tubular portion 47 of catheter 46 surrounding its length is inserted into the vein. While catheter 46 and protective sheath 40 are held stationary, base 43 of needle 32 is drawn rearward with protective sheath member 40 still engaged with base 48 of catheter 46.

Figure 16:
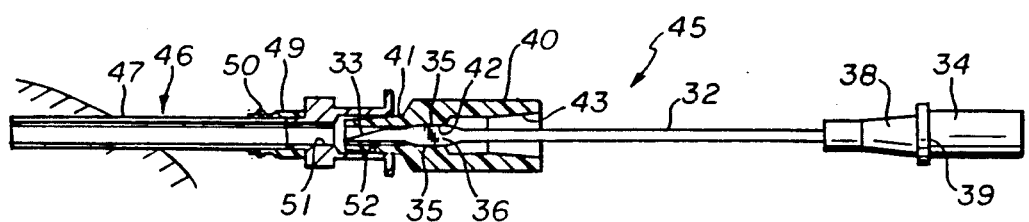
FIG. 16 is a longitudinal cross section of the catheter-needle embodiment of FIG. 14 shown with the needle being removed and the catheter remaining in place.

As needle 32 is completely withdrawn from catheter 46, projections 35 on the forward portion of needle 32 slide through tubular portion 47 and base 48 of catheter 46 and become frictionally engaged in interior bore 42 at the forward end of protective sheath member 40 and pull it out of catheter base member 48 as the needle is removed (FIG. 16). Thus, as needle 32 is removed, protective sheath member 40 is caused to assume its forward protective position covering beveled end 33 of needle 32 and it can be safely handled and disposed of without the danger of accidental pricking or reuse.

Figure 17:
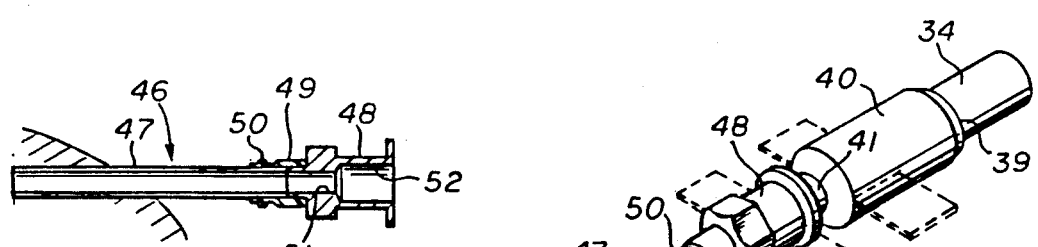
FIG. 17 is a longitudinal cross section of the catheter-needle embodiment of FIG. 14 showing the catheter in place after the needle has been completely removed.

As seen in FIG. 17, after needle 32 is removed, only flexible tubular portion 47 of catheter 46 remains beneath the skin, the proper connections are made at base 48 of the catheter, and it may be secured in place by tape or other conventional means. By completely withdrawing the needle, the catheter has unobstructed fluid flow through its interior. After catheter 46 is removed from the patient, removable sheath 53 may be reinstalled over flexible tubular portion 47 and the used catheter properly disposed of.

Figure 18:
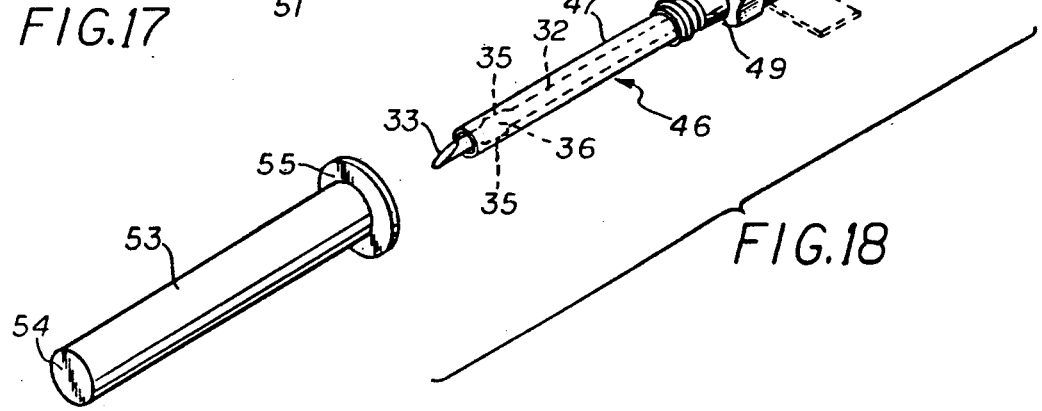
FIG. 18 is an isometric view of the catheter-needle embodiment of FIG. 14 showing the removable sheath removed.

FIG. 18 shows a "butterfly" modification of the catheter-needle embodiment wherein base 48 of catheter 46 and/or the retractable sheath 40 each may have a pair of opposed flexible "wings" or tabs 56 extending laterally outward from their exterior diameters. The tabs 56 provide a flat surface to facilitate securing the catheter and/or protective sheath member to the patient with tape. Each pair of flexible tabs 56 may be bent upward and pinched together with the fingertips to facilitate handling. As previously shown and described with reference to FIG. 13, one pair of the flexible tabs may also be sized to overlap the other whereby they may be bent and pinched together as a single pair.

While this invention has been described fully and completely with special emphasis upon a preferred embodiment, it should be understood that within the scope of the appended claims the invention may be practiced otherwise than as specifically described herein.

I claim:
1. A sheathed hypodermic needle comprising
   a tubular fluid handling needle having a front end adapted for hypodermic penetration and a rear end adapted for connection to fluid ejection or withdrawal means,
   protrusions on the exterior forward portion of said needle formed by flattening a portion of said needle near its front end to cause a portion of the needle exterior diameter to protrude outward sufficient to frictionally engage the interior of said sheath while allowing unobstructed fluid flow through the needle interior,
   a retractable sheath slidably mounted on said needle and movable relative thereto between a rearward retracted position exposing the front end of said needle and a forward protective position enclosing the front end of said needle to prevent inadvertent injury by contact with said needle and to facilitate disposal of said needle,
   the interior of said sheath adapted to frictionally engage said protrusions in said forward protective position and cover the front end of said needle.

2. A sheathed hypodermic needle according to claim 1 in which said retractable sheath comprises a tubular member coaxially surrounding a portion of said needle and having a back end adapted to be slidably received and frictionally engaged on said needle rear base portion, and said sheath slidable axially rearward relative to said needle upon application of axial force to allow the front end of said needle to protrude beyond the front end of said sheath for hypodermic penetration and to engage said sheath on said needle rear base portion.

3. A sheathed hypodermic needle according to claim 2 in which said sheath back end having a central bore which is capable of being slidably received and frictionally engaged on said needle rear base portion.

4. A sheathed hypodermic needle according to claim 1 in which said sheath is frictionally engaged on said needle protrusions in the forward protective position whereby relative longitudinal movement between said needle and said sheath is prevented while allowing rotational movement as a single unit about their longitudinal axis to facilitate connection of said needle base to fluid ejection or withdrawal means.

5. A sheathed hypodermic needle according to claim 1 in which said sheath has a pair of flat flexible tabs extending outwardly from its exterior in laterally opposed relation to facilitate securing said needle to the patient.

6. A sheathed hypodermic needle according to claim 1 in which said needle base has a pair of flat flexible tabs extending outwardly from its exterior in laterally opposed relation to facilitate securing said needle to the patient.

7. A sheathed hypodermic needle comprising a tubular fluid handling needle having a front end adapted for hypodermic penetration and a rear end adapted for connection to fluid ejection or withdrawal means, protrusions on the exterior forward portion of said needle, a retractable sheath slidably mounted on said needle and movable relative thereto between a rearward retracted position exposing the front end of said needle and a forward protective position enclosing the front end of said needle to prevent inadvertent injury by contact with said needle and to facilitate disposal of said needle, the interior of said sheath adapted to frictionally engage said protrusions in said forward protective position and cover the front end of said needle, said needle base has a pair of flat flexible tabs extending outwardly from its exterior in laterally opposed relation, and said sheath has a pair of flat flexible tabs extending outwardly from its exterior in laterally opposed relation to facilitate securing said needle to the patient.

8. A sheathed hypodermic needle according to claim 1 including a tubular fluid handling catheter slidably received on said needle and having a flexible tubular front portion closely surrounding the front portion of said needle and said protrusions and leaving said needle front end exposed for hypodermic penetration therewith and a rear base portion adapted for removable connection to said retractable sheath for axial movement therewith or for connection to fluid ejection or withdrawal means, whereby when said retractable sheath is in its rear position and said catheter is connected to said retractable sheath, the front portion of said needle and said catheter may be hypodermically inserted into a subject as a single unit, and after insertion, said needle may be withdrawn until said retractable sheath is in its forward protective position covering the front end of said needle and said retractable sheath and said needle may be disconnected and removed from said catheter base to leave only said catheter hypodermically installed into the subject, and after said retractable sheath and said needle are removed, said catheter base may be connected to fluid ejection or withdrawal means.

9. A sheathed hypodermic needle according to claim 8 in which said retractable sheath comprises a tubular member coaxially surrounding a portion of said needle and having a front end adapted to be slidably received and frictionally engaged on said catheter rear base portion, and said catheter rear base portion having a central bore which is capable of being slidably received and frictionally engaged on said retractable sheath front end.

10. A sheathed hypodermic needle according to claim 8 including a removable tubular protective sheath having an enclosed front end and an open back end adapted for removable connection to said catheter base to surround and enclose the forward portion of said catheter and said needle front end when said needle and catheter is not in use.

11. A sheathed hypodermic needle according to claim 10 in which said catheter has an intermediate portion between its base and its tubular portion, and the interior of said tubular removable sheath back end is adapted to frictionally engage said intermediate portion in its connected condition.

12. A sheathed hypodermic needle according to claim 8 in which said catheter base has a pair of flat flexible tabs extending outwardly from its exterior in laterally opposed relation to facilitate securing said catheter to the subject.

13. A sheathed hypodermic needle according to claim 8 in which said sheath has a pair of flat flexible tabs extending outwardly from its exterior in laterally opposed relation to facilitate securing said needle to the subject.

14. A sheathed hypodermic needle according to claim 8 in which said catheter base has a pair of flat flexible tabs extending outwardly from its exterior in laterally opposed relation, and said sheath has a pair of flat flexible tabs extending outwardly from its exterior in laterally opposed relation to facilitate securing said catheter and needle to the subject.

* * * * *